United States Patent [19]
Bielefeldt et al.

[11] Patent Number: 5,672,787
[45] Date of Patent: Sep. 30, 1997

[54] PROCESS FOR PREPARING 1,1,1,4,4,4-HEXAFLUOROBUTANE IN THE LIQUID PHASE

[75] Inventors: Dietmar Bielefeldt, Ratingen; Norbert Lui, Köln; Albrecht Marhold, Leverkusen, all of Germany

[73] Assignee: Bayer Aktiengesellschaft, Leverkusen, Germany

[21] Appl. No.: 664,877

[22] Filed: Jun. 17, 1996

Related U.S. Application Data

[63] Continuation of Ser. No. 456,894, Jun. 1, 1995, abandoned.

[30] Foreign Application Priority Data

Jun. 21, 1994 [DE] Germany .................. 44 21 702.1

[51] Int. Cl.$^6$ .................................................. C07C 19/08
[52] U.S. Cl. .................................................. 570/175
[58] Field of Search .................................. 570/175

[56] References Cited

U.S. PATENT DOCUMENTS 4,902,839  2/1990  Bielefeldt et al. ............... 570/175

FOREIGN PATENT DOCUMENTS

| | | |
|---|---|---|
| 442087 | 8/1991 | European Pat. Off. . |
| 587896 | 3/1994 | European Pat. Off. . |
| 3735467 | 5/1989 | Germany . |
| 6228023 | 8/1994 | Japan ................... 570/175 |

OTHER PUBLICATIONS

Agricultural Chemistry—p. 8, JP06228023–A, "Prodn. of 1,1,1,4,4,4–hexa . . . " Apr. 24, 1991.

Derwent Database, AN 93–232277, abstract of JP05-155,788, (1993).

A Henne, J. Am. Chem. Soc., vol. 71, p. 298 (1949).

*Primary Examiner*—Alan Siegel
*Attorney, Agent, or Firm*—Sprung Horn Kramer & Woods

[57] ABSTRACT

1,1,1,4,4,4-Hexafluorobutane (R 356) can be obtained in a simple manner and in excellent yields and with excellent selectivities when 1,1,1,4,4,4-hexafluorobutene is reacted in the liquid phase with hydrogen in the presence of a noble metal catalyst.

8 Claims, No Drawings

PROCESS FOR PREPARING 1,1,1,4,4,4-HEXAFLUOROBUTANE IN THE LIQUID PHASE

This application is a continuation of application Ser. No. 08/456,894, filed Jun. 1, 1995 now abandoned.

The present invention relates to a particularly selective process for preparing 1,1,1,4,4,4-hexafluorobutane (R 356) from 1,1,1,4,4,4-hexafluorobutene by hydrogenation.

It is already known that K 356 can be prepared by liquid-phase hydrogenation of chlorine-containing hexafluorobutenes or chlorine-free hexafluorobutine (see Y. Huang et al., Youji Huaxve 2 125 (1984) and DE-A 3 735 467, which corresponds to U.S. Pat. No. 4,902,839). Chlorine-containing hexafluorobutenes here give hydrogen chloride which has to be removed as salt with the aid of a base. The removal of the salt and its further disposition requires special effort. In addition, the reaction product always still contains a considerable proportion of chlorine-containing products.

A disadvantage of the use of hexafluorobutine is that it is difficult and costly to obtain.

Furthermore, a liquid-phase process is known in which, likewise starting from hexafluorobutine, K 356 is obtained (J.A.C.S. 71 298 (1949)). Besides the fact that hexafluorobutine is difficult to obtain, it is a disadvantage that here K 356 is only obtained in yields of at most 27% of theory.

There is thus still the need for a process by means of which K 356 can be obtained from readily available starting materials in good yields and without disposal of byproducts.

A process has now been found for preparing 1,1,1,4,4,4,-hexafluorobutane (R 356) which is characterized in that 1,1,1,4,4,4-hexafluorobutene is reacted in the liquid phase with hydrogen in the presence of a noble metal catalyst.

1,1,1,4,4,4-Hexafluorobutene is readily obtainable from 1,1,1,4,4-pentafluoro-3,4-dichlorobutane by simultaneous fluorination and elimination.

The process of the invention is carried out at such combinations of pressure and temperature that the reaction mixture (with the exception of the catalyst) is essentially present in the liquid phase. Within this proviso, the pressure can be varied, for example, within the range from 0.5 to 300 bar and the temperature can be varied, for example, within the range from 0 to 250 C. Since 1,1,1,4,4,4-hexafluorobutene boils at 9 C. at atmospheric pressure and 1,1,1,4,4,4-hexafluorobutane boils at 25 C. at atmospheric pressure, the reaction is frequently carried out at elevated pressure. Preference is given to temperatures in the range from 20 to 120 C. and pressures in the range from 2 to 100 bar.

The process of the invention can optionally be carried out in the presence of solvents. Examples of solvents which can be used here are alcohols, ethers and hydrocarbons. Preferably, however, no solvents are added.

The molar ratio of hydrogen to 1,1,1,4,4,4-hexafluorobutene used can be, for example, from 100 to 1:1. It is preferably in the range from 10 to 2:1.

The noble metal catalyst can be, for example, noble metals and/or noble metal compounds of transition groups VII and/or VIII of the Periodic Table of the Elements. These can optionally be arranged on a support, for example on silica, aluminium oxide, spinels, silicates or carbons. Suitable noble metal compounds are, in particular, oxides, hydroxides and hydrated oxides. Preference is given to noble metals and noble metal compounds of transition group VIII of the Periodic Table of the Elements, in particular metallic palladium on one of the specified support materials.

Based on 1,1,1,4,4,4-hexafluorobutene, use can be made, for example, of from 0.001 to 5% by weight of catalyst (calculated as metal). This mount is preferably from 0.05 to 1% by weight.

The process of the invention can be carried out continuously or batchwise. It can be carried out batchwise, for example, in a pressure vessel. After the reaction is complete, excess hydrogen can be separated from other constituents of the reaction mixture by decompression and can optionally be re-used. The catalyst can, for example, be separated off by filtration (optionally under pressure) or by vaporization of the vaporizable components of the reaction mixture (=virtually pure 1,1,1,4,4,4-hexafluorobutane). In this way, 1,1,1,4,4,4-hexafluorobutane is generally obtained in purifies and yields of above 95%, frequently in purifies above 99% and almost quantitative yields.

In the continuous mode of operation, the reaction can be carried out, for example, in one or more reactors connected in series, for example a cascade reactor, which contain the catalyst and to which 1,1,1,4,4,4-hexafluorobutene and hydrogen are fed and from which volatile components of the reaction mixture are taken. The catalyst can remain in the reactors, the excess hydrogen can be separated off by decompression and circulated. 1,1,1,4,4,4-Hexafluorobutane is then obtained in purities and yields as in the batchwise procedure.

A suitable material for the reaction vessels is, for example, stainless steel. It is generally advantageous to condition reaction vessels of stainless steel prior to their being used, for example by treatment with nitric acid.

In both cases (continuous and batchwise operation), the heat of reaction can be utilized to vaporize the product from the catalyst. A further purification of the 1,1,1,4,4,4-hexafluorobutane thus prepared and isolated is generally not necessary.

The process of the invention has a series of advantages; virtually no byproducts which need to be disposed of, such as hydrogen chloride or salts, are formed, it starts out from readily available starting materials, it gives a 1,1,1,4,4,4-hexafluorobutane (R 356) in excellent yields and with excellent selectivities, the reaction mixture can be worked up in a simple manner since virtually only excess hydrogen and the catalyst have to be removed from the product, and it requires no added materials such as bases.

EXAMPLES

Example 1

In a 20 l stainless steel autoclave, which had previously been conditioned using 10% strength nitric acid and was equipped with closed circuit heating and an anchor stirrer, 10.0 kg of 1,1,1,4,4,4-hexafluorobutene were heated from 0 to 30 C. over a period of 10 minutes in the presence of 250 g of catalyst (5% by weight of metallic palladium on activated carbon) at a pressure of 20 bar of hydrogen. After reaching this temperature, the hydrogen consumption was compensated for by repeated pressurization with fresh hydrogen at pressures between 20 and 30 bar. After about 2.5 hours the conversion was 87%. 1,1,1,4,4,4-Hexafluorobutane had been formed in a yield of greater than 99% of theory.

Example 2

The procedure was similar to Example 1, but the hydrogenation was carried out at 50 C. and after hydrogen uptake was complete the mixture was stirred for a further 3 hours at 50 C. 1,1,1,4,4,4-Hexafluorobutane was then separated from the catalyst by pressure filtration. At a conversion of above 99.8%, 1,1, 1,4,4,4-hexafluorobutane was obtained virtually quantitatively.

Example 3

The procedure was similar to that in Example 1, but the hydrogenation was carried out at 70 C. and at pressures of from 40 to 60 bar of hydrogen. After hydrogen uptake was complete, the mixture was stirred for a further 1 hour at 70 C. 1,1,1,4,4,4Hexafluorobutane was then separated from the catalyst by pressure filtration. The 1,1,1,4,4,4-hexafluorobutene had been converted virtually quantitatively.

What is claimed is:

1. A process for preparing 1,1,1,4,4,4-hexafluorobutane (R 356) which comprises reacting 1,1,1,4,4,4-hexafluorobutene in the liquid phase with hydrogen in the presence of a noble metal catalyst and in the absence of a solvent, in a stainless steel reaction vessel which, prior to its use, is treated with nitric acid, and wherein a product is produced with a purity of over 99% and at a yield above 99%.

2. The process of claim 1, which is carried out at such combinations of pressure and temperature that the reaction mixture is essentially present in the liquid phase at pressures in the range from 0.5 to 300 bar and at temperatures in the range from 0 to 250 C.

3. The process of claim 1, in which the molar ratio of hydrogen to 1,1,1,4,4,4-hexafluorobutene used is from 100 to 1:1.

4. The process of claim 1, in which the noble metal catalyst is selected from the group consisting of noble metals and noble metal compounds of transition group VII and/or VIII of the Periodic Table of the Elements.

5. The process of claim 1, in which the noble metal catalyst is arranged on a support.

6. The process of claim 1, in which from 0.001 to 5% by weight of noble metal catalyst (calculated as metal) is used.

7. The process of claim 1, which is carried out continuously.

8. The process of claim 1, which is carried out batchwise.

* * * * *